United States Patent [19]
Deily et al.

[11] Patent Number: 5,993,412
[45] Date of Patent: Nov. 30, 1999

[54] INJECTION APPARATUS

[75] Inventors: Michael F. Deily; James J. Bunch, both of Tigard; Thomas J. Drach, Hood River; James M. Bonicatto, Portland, all of Oreg.

[73] Assignee: Bioject, Inc., Portland, Oreg.

[21] Appl. No.: 08/858,249

[22] Filed: May 19, 1997

[51] Int. Cl.$^6$ .................................................. A61M 5/30
[52] U.S. Cl. ........................... 604/68; 604/72; 604/187; 604/140
[58] Field of Search ................... 128/DIG. 1; 604/50, 604/65, 67, 68, 70, 71, 98, 111, 131, 143, 146, 147, 208–210, 246

[56] References Cited

U.S. PATENT DOCUMENTS

| | | | |
|---|---|---|---|
| D. 277,506 | 2/1985 | Ibis | D24/24 |
| D. 316,899 | 5/1991 | Andersson et al. | D24/24 |
| D. 330,079 | 10/1992 | Dalling et al. | D24/24 |
| D. 349,958 | 8/1994 | Hollis et al. | D24/112 |
| 1,742,497 | 1/1930 | Dickinson . | |
| 2,025,219 | 12/1935 | Smith . | |
| 2,101,140 | 12/1937 | Hege . | |
| 2,322,245 | 6/1943 | Lockhart . | |
| 2,380,534 | 7/1945 | Lockhart . | |
| 2,547,009 | 4/1951 | Smoot . | |
| 2,605,763 | 8/1952 | Smoot . | |
| 2,653,602 | 9/1953 | Smoot . | |
| 2,680,439 | 6/1954 | Sutermeister . | |
| 2,688,968 | 9/1954 | Scherer . | |
| 2,704,543 | 3/1955 | Scherer . | |
| 2,714,887 | 8/1955 | Venditty . | |
| 2,737,946 | 3/1956 | Hein, Jr. . | |
| 2,754,818 | 7/1956 | Scherer . | |
| 2,764,977 | 10/1956 | Ferguson . | |
| 2,816,543 | 12/1957 | Venditty et al. . | |
| 2,821,193 | 1/1958 | Ziherl et al. . | |
| 2,821,981 | 2/1958 | Ziherl et al. . | |
| 2,902,995 | 9/1959 | Loper . | |
| 3,110,309 | 11/1963 | Higgins . | |
| 3,130,723 | 4/1964 | Venditty et al. . | |

(List continued on next page.)

FOREIGN PATENT DOCUMENTS

| | | |
|---|---|---|
| 2627698 | 3/1988 | France . |
| 1047562 | 11/1966 | United Kingdom . |
| 87/03494 | 6/1987 | WIPO . |
| 90/15633 | 12/1990 | WIPO . |

*Primary Examiner*—Wynn Wood Coggins
*Assistant Examiner*—Sharon Finkel
*Attorney, Agent, or Firm*—Kolisch Hartwell Dickinson McCormack & Heuser

[57] ABSTRACT

The present invention typically is in the form of a needleless injector which includes the following components: (1) a needleless syringe installed in the injector for holding medication prior to injection, the syringe including an injection aperture at the forward end thereof; (2) a syringe plunger slidably mounted to the rear end of the syringe for forcing medication out the syringe aperture; (3) a syringe plunger drive mechanism providing power to drive the syringe plunger and thereby force medication out of the syringe; and (4) a syringe drive control mechanism for controlling the operation of the drive mechanism, the drive control mechanism including a warning system which warns the user if a pre-injection condition is not met, an interlock system which prevents injection from taking place if the pre-injection condition is not met, and a sensing system which senses whether the pre-injection condition is not met and conveys a signal to the warning and interlock systems informing as to whether the pre-injection condition is met.

24 Claims, 10 Drawing Sheets

5,993,412
Page 2

U.S. PATENT DOCUMENTS

| | | |
|---|---|---|
| 3,167,071 | 1/1965 | Venditty . |
| 3,179,107 | 4/1965 | Clark . |
| 3,292,621 | 12/1966 | Banker . |
| 3,292,622 | 12/1966 | Banker . |
| 3,424,154 | 1/1969 | Kinsley . |
| 3,490,451 | 1/1970 | Yahner . |
| 3,515,130 | 6/1970 | Tsujino . |
| 3,557,784 | 1/1971 | Shields . |
| 3,561,443 | 2/1971 | Banker . |
| 3,688,765 | 9/1972 | Gasaway . |
| 3,695,266 | 10/1972 | Lussier . |
| 3,714,943 | 2/1973 | Yanof et al. . |
| 3,802,430 | 4/1974 | Schwebel et al. . |
| 3,853,125 | 12/1974 | Clark et al. . |
| 3,855,380 | 12/1974 | Gordon et al. . |
| 3,945,379 | 3/1976 | Pritz et al. . |
| 3,945,383 | 3/1976 | Bennett et al. . |
| 4,059,107 | 11/1977 | Iriguchi et al. . |
| 4,124,024 | 11/1978 | Schwebel et al. . |
| 4,252,159 | 2/1981 | Maki . |
| 4,266,541 | 5/1981 | Landau . |
| 4,284,459 | 8/1981 | Patel et al. . |
| 4,329,988 | 5/1982 | Sarnoff et al. . |
| 4,403,989 | 9/1983 | Christensen et al. . |
| 4,421,508 | 12/1983 | Cohen . |
| 4,475,905 | 10/1984 | Himmelstrup ............... 604/208 |
| 4,507,113 | 3/1985 | Dunlap . |
| 4,516,967 | 5/1985 | Kopfer . |
| 4,568,346 | 2/1986 | van Dijk . |
| 4,581,014 | 4/1986 | Millerd et al. . |
| 4,592,742 | 6/1986 | Landau . |
| 4,596,556 | 6/1986 | Morrow et al. . |
| 4,623,332 | 11/1986 | Lindmayer et al. . |
| 4,626,242 | 12/1986 | Fejes et al. . |
| 4,680,027 | 7/1987 | Parsons et al. . |
| 4,717,384 | 1/1988 | Waldeisen . |
| 4,722,728 | 2/1988 | Dixon . |
| 4,759,756 | 7/1988 | Forman et al. . |
| 4,790,824 | 12/1988 | Morrow et al. . |
| 4,850,967 | 7/1989 | Cosmai . |
| 4,874,367 | 10/1989 | Edwards . |
| 4,886,495 | 12/1989 | Reynolds . |
| 4,913,699 | 4/1990 | Parsons . |
| 4,940,460 | 7/1990 | Casey et al. . |
| 4,941,880 | 7/1990 | Burns . |
| 4,944,726 | 7/1990 | Hilal et al. . |
| 4,944,736 | 7/1990 | Holtz . |
| 4,966,581 | 10/1990 | Landau . |
| 4,997,430 | 3/1991 | Van der Heiden et al. . |
| 5,009,637 | 4/1991 | Newman et al. . |
| 5,024,656 | 6/1991 | Gasaway et al. . |
| 5,049,125 | 9/1991 | Accaries et al. . |
| 5,062,830 | 11/1991 | Dunlap . |
| 5,064,413 | 11/1991 | McKinnon et al. . |
| 5,073,165 | 12/1991 | Edwards . |
| 5,078,690 | 1/1992 | Ryan . |
| 5,080,648 | 1/1992 | D'Antonio . |
| 5,116,313 | 5/1992 | McGregor . |
| 5,312,335 | 5/1994 | McKinnon et al. . |
| 5,312,577 | 5/1994 | Peterson et al. . |
| 5,318,522 | 6/1994 | D'Antonio . |
| 5,383,851 | 1/1995 | McKinnon, Jr. et al. . |
| 5,399,163 | 3/1995 | Peterson et al. . |
| 5,466,220 | 11/1995 | Brenneman . |
| 5,472,022 | 12/1995 | Michel et al. . |
| 5,480,381 | 1/1996 | Weston . |
| 5,503,627 | 4/1996 | McKinnon et al. . |
| 5,505,697 | 4/1996 | McKinnon, Jr. et al. . |
| 5,520,639 | 5/1996 | Peterson et al. . |

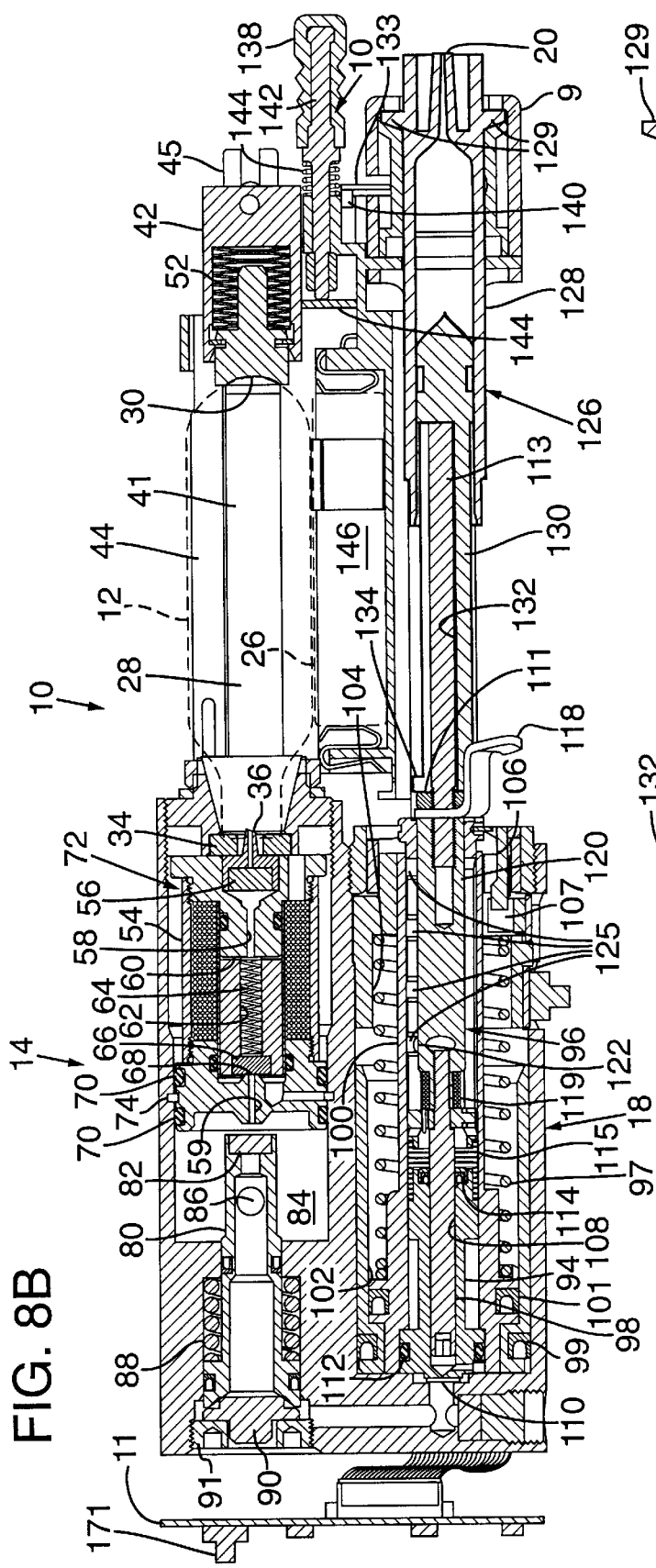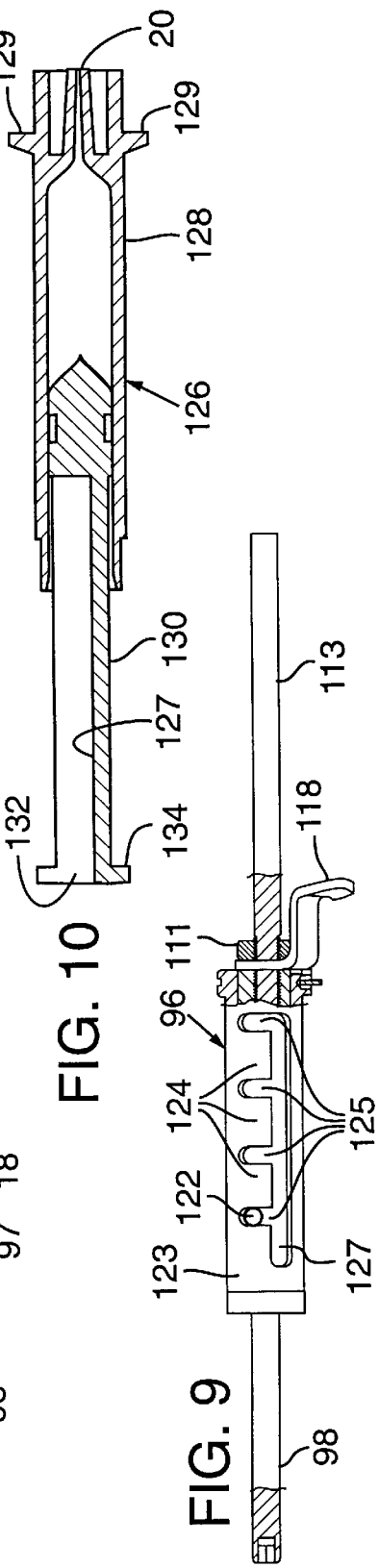

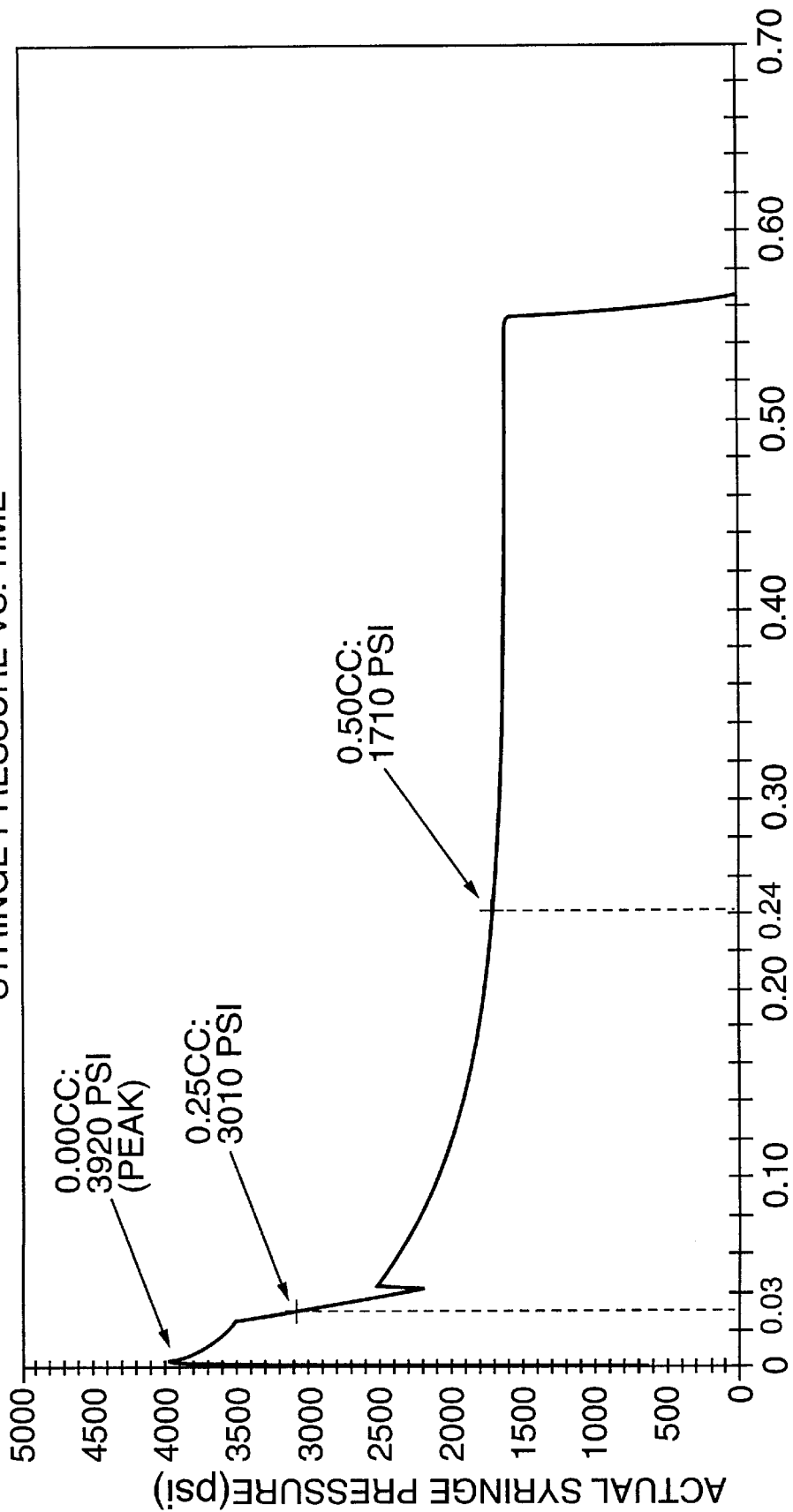

INJECTION APPARATUS

BACKGROUND OF THE INVENTION

This invention relates to a needle-free or needleless hypodermic injection device used to subcutaneously inject medication into the skin of a patient.

There are many attributes which are highly desirable in an injection system, whether it is of the type that uses a needle and syringe, or is of needleless configuration. It is necessary to accurately meter a dose, and to permit the dose to be varied from injection to injection. It is also highly desirable that the injection system be capable of use by the patients themselves, and be usable by someone with limited physical capabilities. For example, physically disabled patients are often in need of regular medication. Some patients have particular difficulty with motor control, and yet to live an independent life, they need to be able to self-administer injections. Needleless injection systems are suitable for these types of patients because one of the common problems is that it is difficult for them to grasp and manipulate a smaller object such as a syringe. It is also desirable that the system can be used, that is, loaded, manipulated, and administered, by one who has had no medical training and who has had little training or experience in the use of the injection system.

In a needleless injection system, there are a number of attributes which need to be considered which are not necessarily present when a conventional syringe and needle-type system is used. For example, the needleless injection system needs to be positioned directly against and roughly perpendicular to the skin of the patient. This is not a factor when the skin is being pierced with a needle. Also, any needleless injection system using compressed gas needs to have adequate compressed gas loading pressure in order to prevent misfiring or improper application of medication. Moreover, the loading of pressure within the injection system needs to be performed in a predictable, repeatable fashion so that the pressure is precisely loaded. Some existing equipment includes a turn down screw which pierces a compressed gas vessel. But during the turning down operation, gas pressure is lost, and the amount of lost pressure varies directly with the rate at which the screw is turned. This will normally not affect the proper operation of the injector, but it may well reduce the number of injections possible with a single cartridge.

Another desirable feature in needleless injection systems is that the units be relatively inexpensive, be virtually maintenance free, and be able to last for an appropriate period of time. Not only are patients who utilize these products often supported by fixed incomes, but because they are often disabled, they may not recognize that there is a problem with a unit which is prone to breakdown or which needs regular maintenance. Therefore, reliability is an important advantage, as well as the ease of use previously discussed.

One problem which exists with some of the prior injection systems is that it is difficult to fill the ampule with a precise measurement of medication in a process which is simple and which, again, may be performed by someone who has difficulty handling small objects or who is otherwise disabled.

One of the drawbacks with some conventional gas powered injection devices is that the gas pressure acting upon the unit may rise too slowly, so that the medication initially ejected from the injector does not have sufficient pressure or velocity to pass through the skin. In that instance, it is possible that a portion of the medication will splash back onto the patient, so that the patient does not receive a full dose. In these instances, it is virtually impossible to determine how much of a particular dose has been injected, so the user, who is typically unskilled and not very knowledgeable in these systems, may not be able to determine whether another injection is necessary. This therefore results in the patient either being undertreated, or perhaps even causing an overdosage in the event the patient unnecessarily repeats an injection.

Another drawback with prior injection systems, including those which are needleless, is that a number of conditions have to be satisfied for the system to work properly. It would be helpful if the user is given some warning if one or more of the conditions is not satisfied. While an interlock could prevent the system from firing in those circumstances, it would be even more helpful if the user was given some sort of warning prior to attempting to initiate the injections. Such warnings are typically not provided in prior art injection systems.

SUMMARY OF THE INVENTION

The present invention typically is in the form of a needleless injector which includes the following components: (1) a needleless syringe installed in the injector for holding medication prior to injection, the syringe including an injection aperture at the forward end thereof; (2) a syringe plunger slidably mounted to the rear end of the syringe for forcing medication out the syringe aperture; (3) a syringe plunger drive mechanism providing power to drive the syringe plunger and thereby force medication out of the syringe; and (4) a syringe drive control mechanism for controlling the operation of the drive mechanism, the drive control mechanism including a warning system which warns the user if a pre-injection condition is not met, an interlock system which prevents injection from taking place if the pre-injection condition is not met, and a sensing system which senses whether the pre-injection condition is not met and conveys a signal to the warning and interlock systems informing as to whether the pre-injection condition is met.

Another aspect of the invention is a needleless injection system which includes a needleless syringe including an ampule for holding medication to be injected, and a plunger reciprocable with respect to the ampule for drawing medication into and forcing the medication from the ampule; a syringe drive mechanism for providing power to drive the syringe plunger to force medication out of the syringe ampule, the drive mechanism operable to provide a first level force during a first, short period of injection, and a second, lower level of force during a second, longer period of injection, the second level of force being substantially constant for the second period of injection.

Yet another aspect of the invention provides a needleless, compressed gas powered injector adapted to receive a syringe with medication therein. The injector includes a syringe drive system for providing compressed gas drive to the syringe mounted in the injector, and a pressure switch for determining whether the injector has sufficient compressed gas pressure, and for warning the user if there is insufficient pressure and for preventing initiation of the apparatus in the event of insufficient compressed gas pressure.

A further aspect of the invention is a needleless injector adapted to receive a syringe with medication therein for injection, and using an elongated compressed gas cartridge which is pierceable at one end, the gas cartridge providing compressed gas to the injector, the injector including a cartridge access door which opens and closes, and the injector defining a cartridge receptacle for receiving the cartridge, the cartridge receptacle having a first end and a second end, the first end of which terminates in a piercing pin for piercing the cartridge, the second end of which terminates in a seat, with at least one of the piercing pin and the seat moving away from the other with the opening of the door and toward the other with the closing of the door, the piercing pin and the seat being positioned relative to each other and with respect to the size of the cartridge such that when the door is open, the receptacle is longer than the cartridge, and when the door is closed, the cartridge will be pierced.

Another aspect of the invention is a needleless, compressed gas powered injector for injecting medication through a syringe, the injector including a dose adjustment mechanism interconnected with a dose compensator, the dose compensator defining a chamber which is enlarged and reduced in size as the amount of medication is reduced and increased, respectively, the dose compensator chamber receiving compressed gas when the injector injects medication.

BRIEF DESCRIPTION OF THE DRAWINGS

FIG. 8B is a view corresponding to FIG. 8, showing the syringe mounted in place in the apparatus;

FIG. 9 is partially sectioned side elevation view of the dose adjustment mechanism of the embodiment of FIG. 1;

FIG. 10 is a side elevation sectional view of the syringe to be used with the embodiment of FIG. 1;

FIG. 14 is a graphical depiction of the "syringe pressure vs. time" of the injection cycle.

DETAILED DESCRIPTION OF THE PREFERRED EMBODIMENT

Figure 1:
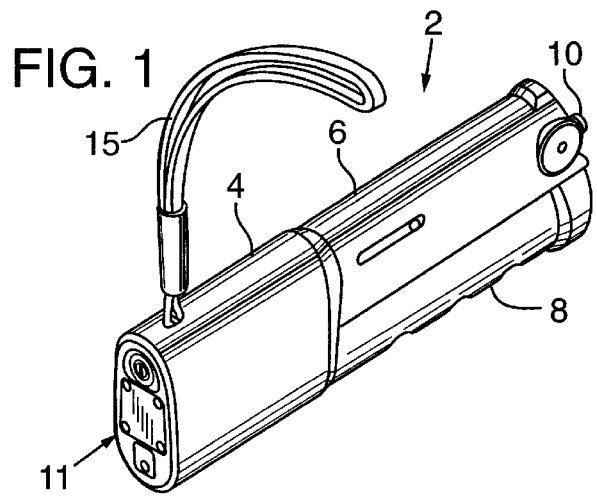
FIG. 1 is a perspective view of the exterior of a first embodiment of the present invention.
Figure 2:
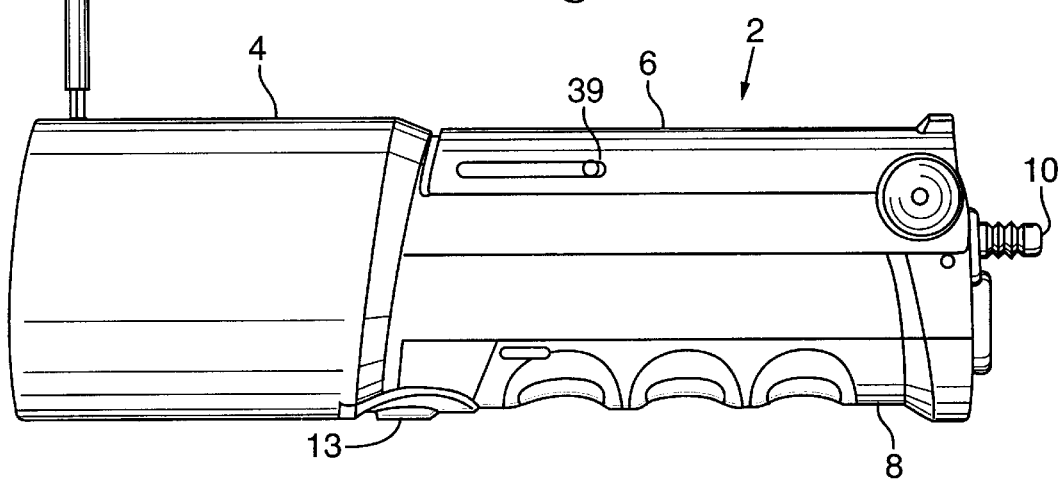
FIG. 2 is a side elevation view of the exterior of the embodiment of FIG. 1.
Figures 3, 4:
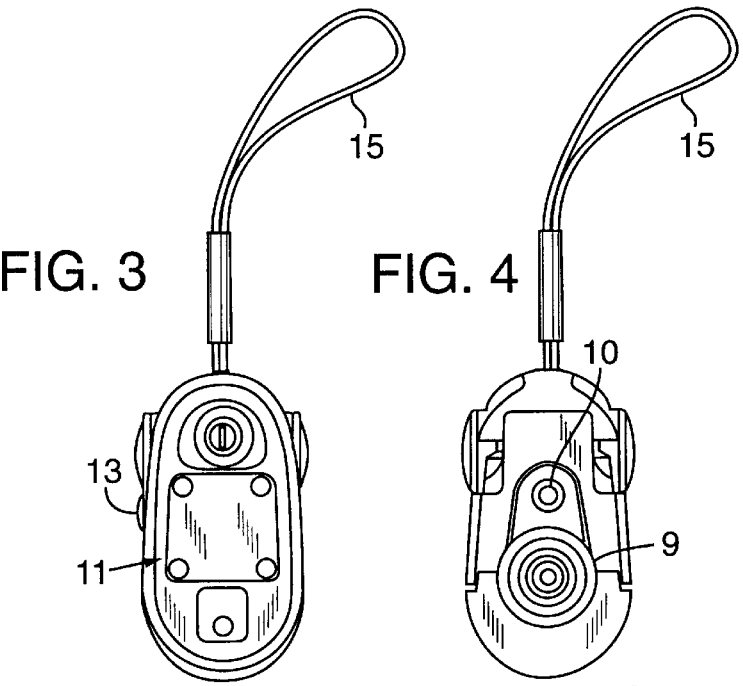
FIG. 3 is a rear end view of the embodiment of FIG. 1, showing the indicator panel.
FIG. 4 is a front end view of the embodiment of FIG. 1, showing the syringe collar and the skin sensor.
Figure 5:
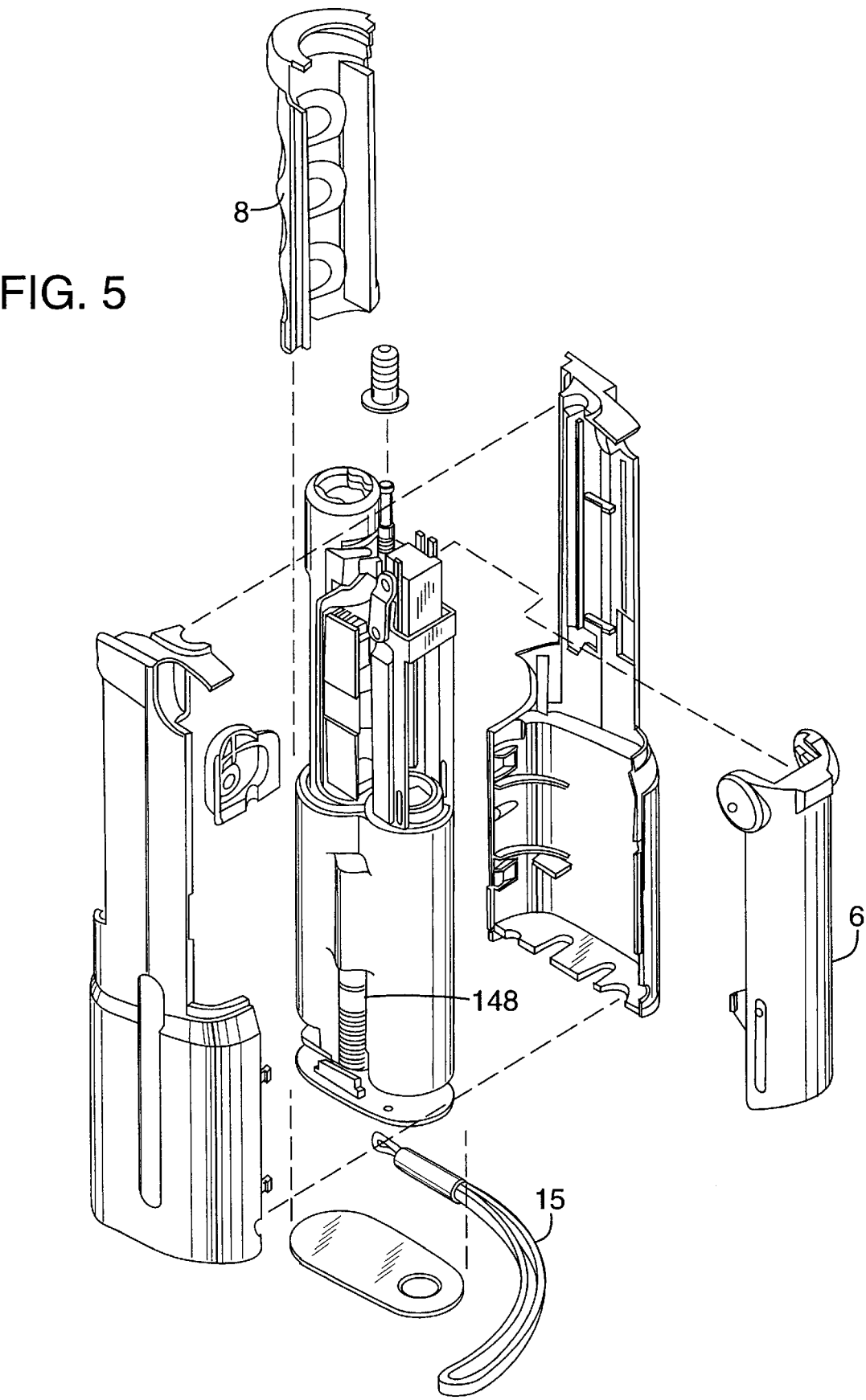
FIG. 5 is an exploded view showing how the external parts of the embodiment of FIG. 1 fit together.

Reference should now be made to the figures which depict a preferred embodiment of the injection apparatus, indicated generally with the numeral 2. Referring first to FIGS. 1–5, it can be seen that apparatus 2 includes a convenient molded plastic case, made up of a base portion 4, a pivotable cartridge access door 6, a slidable dose adjustment door 8, a syringe collar 9, a skin sensor 10, an indicator panel 11, an initiator switch 13, and a carrying strap 15. FIG. 5 depicts how these parts fit together to form an integral unit.

Figure 8:
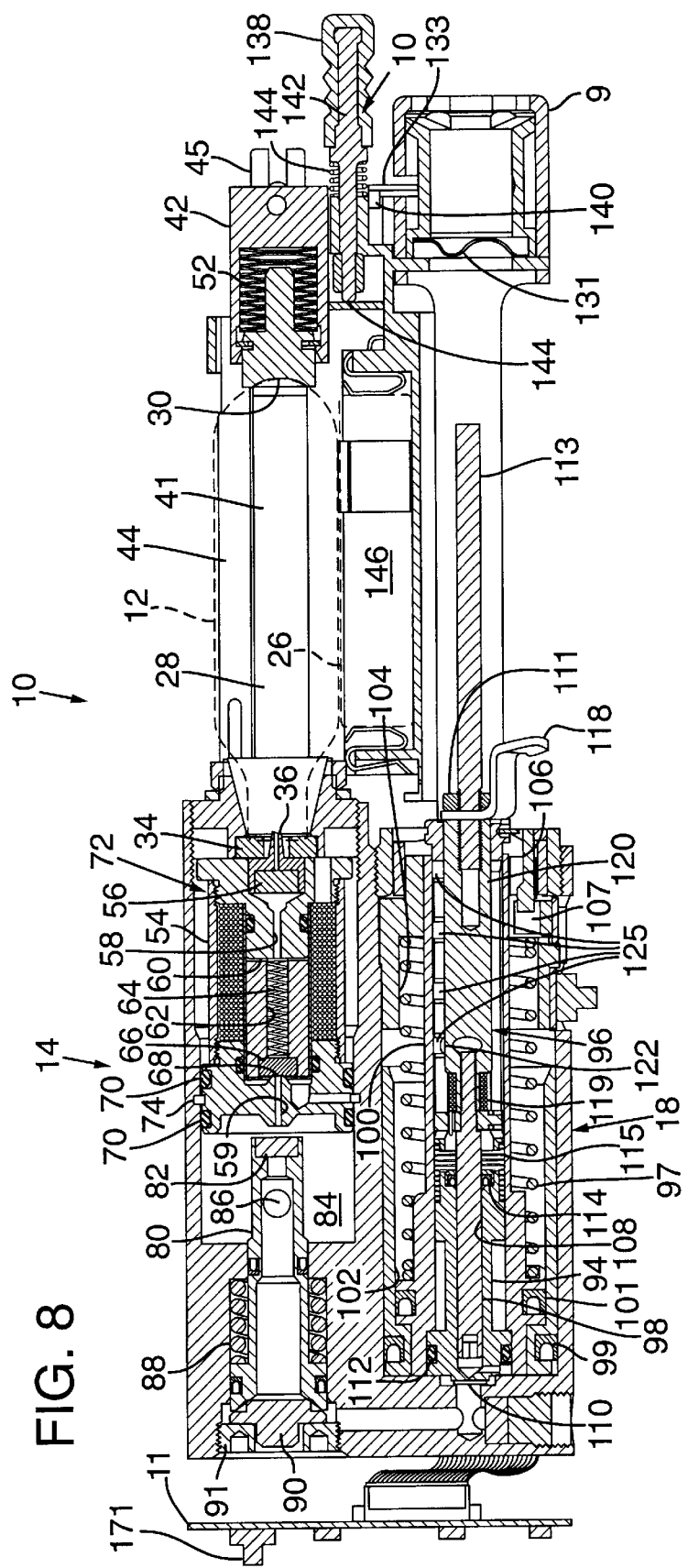
FIG. 8 is a side elevation sectional view of the embodiment of FIG. 1.

Referring now to FIG. 8, apparatus 2 can be seen to include several basic components. First, a replaceable $CO_2$ cartridge 12 is disposed at one side of the apparatus, toward the front. A cartridge pressure control system is shown behind cartridge 12 at 14. As shown best in FIG. 8B, disposed on the other side of the apparatus, at the front thereof, is a syringe 126 which is adapted to hold and then inject a predetermined amount of medication. Positioned rearwardly of the syringe is a syringe control system 18 which controls activation of the syringe. The syringe control system 18 is in turn controlled from pressure which is provided by the cartridge pressure control system 14. Indicator panel 11 is disposed at the rear end of the apparatus, and it includes a power button 171 to activate the apparatus and a series of indicator lamps to keep the operator advised of the condition of the apparatus. Skin sensor 10 is disposed at the front end of the apparatus, and is used to prevent initiation of the injection process unless the skin sensor is depressed an appropriate amount as the apparatus is pressed against the skin of the patient. Finally, a pair of 1.5 volt AAA batteries 26 are mounted in a battery casing 146 disposed between $CO_2$ cartridge 12 and syringe 126 to provide power for the apparatus logic circuit, warning lights, etc. Each of these basic components will now be described in more detail.

The $CO_2$ cartridge 12 is typically a 33 gram steel cartridge of conventional design, holding 8 grams of $CO_2$. This is usually enough for approximately 6–8 injections, although if the apparatus is used infrequently, passive gas leaks may result in fewer injections per cartridge. $CO_2$ cartridge 12 is positioned within a cartridge receptacle 28 between a forward seat 30 which is curved to complement the curvature of the forward, rounded portion of the cartridge, and a rear area having a resilient cartridge sealing gasket 34. This gasket is sized and positioned such that a piercing pin 36 is adapted to extend through an annulus at the axial center of the gasket in order to pierce the rear end of the cartridge 12 to release $CO_2$ pressure upon closure of hinged cartridge access door 6.

Figure 6:
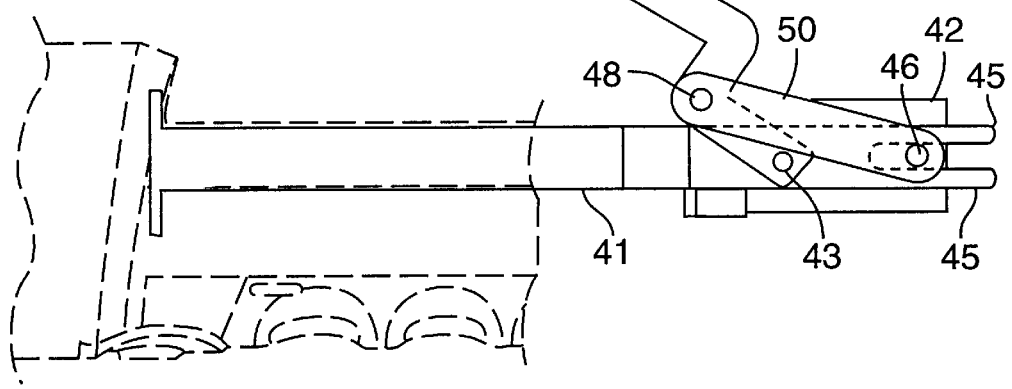
FIG. 6 is a side elevation view of the $CO_2$ cartridge access door closure mechanism of the embodiment of FIG. 1.
Figure 7:
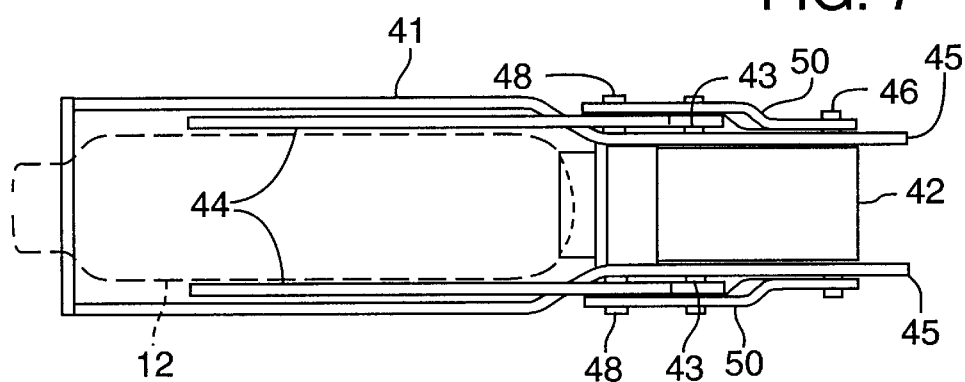
FIG. 7 is a top plan view of the $CO_2$ cartridge access door closure mechanism of the embodiment of FIG. 1.

As seen in FIGS. 6 and 7, hinged cartridge access door 6 is mounted to the ends of a pair of roughly Z-shaped cartridge door closure arms 44 by a pair of small bolts 39 which slide in slots 35 as the door is opened and closed. Cartridge access door 6 is mounted to a so-called pierce block frame 41 and a pierce block 42 by closure arms 44 which straddle the pierce block and are pivotally connected to the pierce block frame at pivot points 43. Pivot points 43 actually are in the form of rivets, and to ensure that the pierce block travels parallel to the pierce block frame, a slot (not shown) extends along each side of the pierce block, and the inner portion of the rivet thereby guides the travel of the pierce block. Closure arms 44 are also pivotally mounted to a pair of pivotal legs 50 disposed to each side of pierce block frame 41 at pivot points 48. The opposite ends of legs 50 pivotally connect to a pierce block pin 46 which extends through and is mounted to pierce block 42. Pivotable legs 50 each include a bend at their mid-portions as shown in FIG. 7 to accommodate the length of closure arms 44. Pierce block pin 46 is mounted to reciprocate in a pair of forked ends 45 in pierce block frame 41 as cartridge access door 6 is opened and closed and pierce block 42 is shifted forwardly and rearwardly. Thus, when cartridge access door 6 is closed, legs 50 convey the motion of closure arms 44 to pierce block pin 46 and to pierce block 42 which shifts within pierce block frame 41. This causes forward seat 30 to exert a rearward force (to the left in FIGS. 6, 7 and 8) on $CO_2$ cartridge 12. As noted above, this causes piercing pin 36 to pierce the rear end of cartridge 12.

As best shown in FIG. 8, a series of 17 so-called belleville spring washers 52 are disposed in series between forward seat 30 and pierce block 42 to provide a predetermined piercing pressure of slightly over 100 pounds, which is maintained the entire time cartridge access door 6 is closed.

Figure 8A:
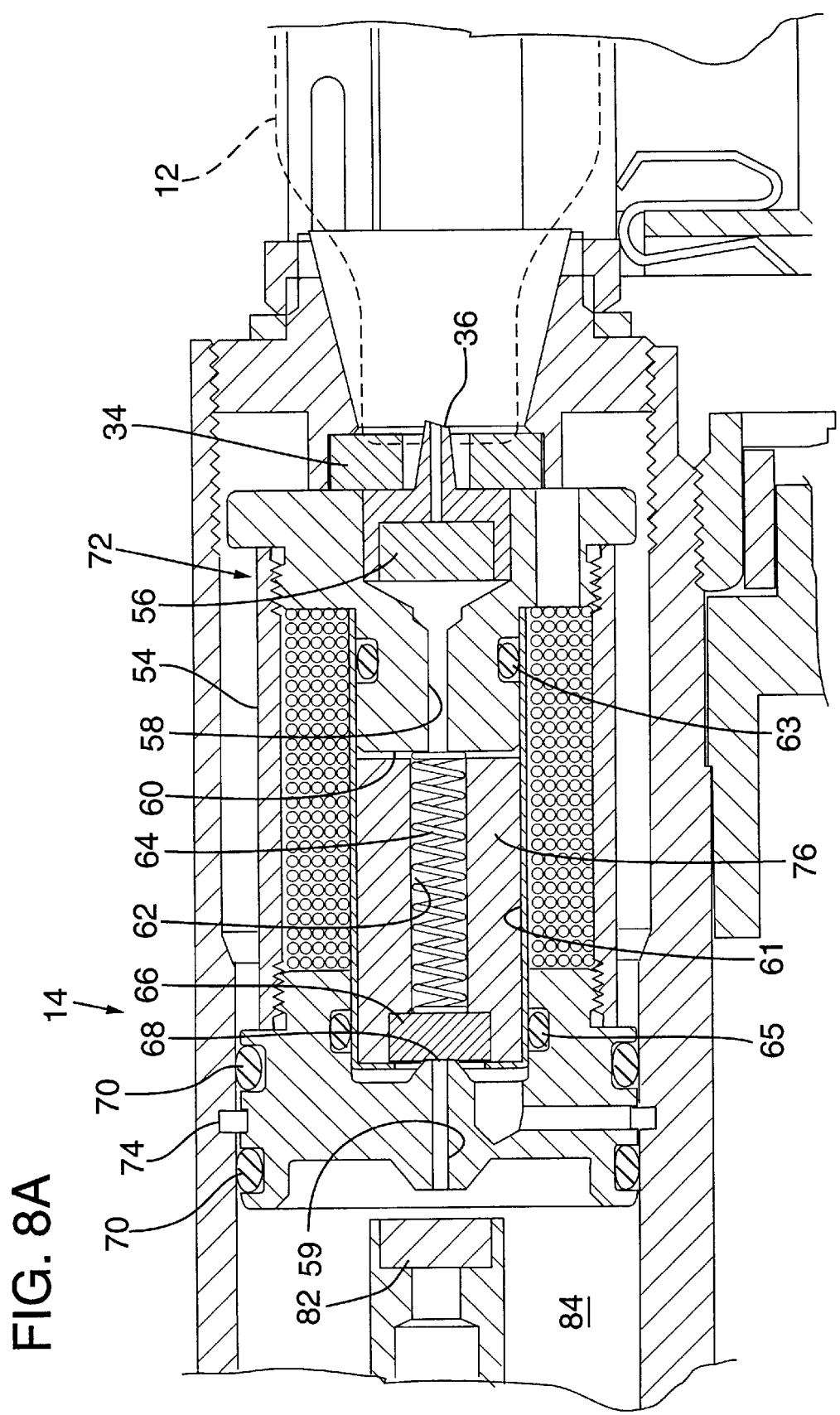
FIG. 8A is a fragmentary, enlarged view corresponding to FIG. 8, showing the solenoid valve components.

Once cartridge 12 has been breached, pressurized $CO_2$ gas passes from the cartridge through piercing pin 36, and as best shown in FIG. 8A, to a solenoid valve 54 through a (0.25×118" 2 micron) gas filter 56 and through a conduit 58 extending through the axial center thereof. A space 60 extending entirely across solenoid valve 54 thus is filled with pressurized gas, as is an axially centered spring chamber 62 in which a solenoid spring 64 is disposed. Solenoid spring 64 holds a resilient solenoid seal 66 against a solenoid seat 68 to prevent the flow of pressure into an axially extending rear conduit 59. A pair of O-rings 70 are mounted in the solenoid valve to prevent flow of pressurized gas along the interior wall 72 of the pressure control system 14. A circumferential ring 74 extends entirely around solenoid valve 54 to ensure that the solenoid valve remains stationary in the pressure control system 14.

A generally cylindrical piston 76 is disposed between space 60 and solenoid seal 66. As will be described below, piston 76, in combination with solenoid seal 66, acts as to control the flow of gas pressure through solenoid valve 54. A sleeve 61 fits around the piston, and well past space 60, and an O-ring 63 prevents $CO_2$ pressure from passing forwardly along the sleeve. Pressure is, however, able to pass rearwardly along the interface between the sleeve and the piston because another O-ring 65, disposed rearwardly of space 60, is positioned outwardly of the sleeve.

The cartridge pressure control system 14 also includes a poppet valve 80 (see FIG. 8) having a resilient poppet valve seal 82 which bumps up against rear conduit 59 to create a shuttling phenomenon when the poppet valve shifts forwardly or to the right, as will be described later in this discussion. Poppet valve 80 includes a radially extending port 86 which interconnects the inner portion of the poppet valve with a gas reservoir 84. Prior to the point that the reservoir is subjected to $CO_2$ pressure, poppet valve 80 will be in the position depicted in FIG. 8. A poppet valve spring 88 holds the poppet valve in the depicted position, with a poppet valve seat 90 disposed against the poppet valve to close the poppet valve.

Upon closure of cartridge access door 6, and with the solenoid valve in the depicted position, pressurized $CO_2$ flows through piercing pin 36 and filter 56 (see FIG. 8A). It is directed through conduit 58 and into space 60 and spring chamber 62, and along the interface between sleeve 61 and piston 76 to the rear of the piston. While the pressure is therefore equalized at the two ends of the piston, because the surface area is greater on the front side of the piston if the surface area of solenoid seal 66 is included, the piston will remain in the position shown in FIGS. 8 and 8A, with the solenoid seal seated firmly against solenoid seat 68, thereby preventing pressure from entering reservoir 84.

Once the apparatus is initiated to inject medication, solenoid valve 54 is shifted slightly (approximately 0.012 inch) forward or to the right in FIGS. 8 and 8A, but not so far as to close off space 60. This enables pressurized gas to flow through rear conduit 59 into gas reservoir 84.

From the gas reservoir, pressurized $CO_2$ flows through port 86 in poppet valve 80 (see FIG. 8). When the increased pressure within the poppet valve causes the upward force on the poppet valve to exceed the rearward or leftward force of poppet valve spring 88, the poppet valve lifts off its seat 90, permitting pressure to rush into the next section of the apparatus. The poppet valve is normally set to lift off of its seat at a pressure of 480 psi. When poppet valve 80 is in this raised position, poppet valve seal 82 bumps up against rear conduit 59. When the poppet valve opens, the pressure in gas reservoir drops, so that the force of poppet valve spring 88 again exceeds the force of pressurized gas, thereby causing the poppet valve to close. This in turn permits the pressure in gas reservoir 84 to immediately increase, lifting the poppet valve again. This phenomenon, called shuttling, continues for a short period of time until the medication is fully injected. Normally the controller closes the solenoid valve 0.8 seconds after it is opened, so that the time of termination of the shuttling is determined by the controller.

The initial rush of pressure followed by shuttling produces a pressure profile which is ideal for a needleless injection system. As shown in FIG. 14, the initial rush of $CO_2$ pressure provides a syringe pressure of approximately 3920 psi to penetrate the patient's skin, followed by a sustained, substantially constant pressure of approximately 1700 psi for about 0.5 seconds during the shuttling phase. The term "substantially constant" as used herein is intended to encompass a variation of from about 2000 psi to 1600 psi as shown in FIG. 14 between the 0.1 and 0.56 second points of the injection cycle. This pressure profile has been found to be superior to some prior art pressure profiles which peak quickly but then drop off sharply. Assuming 1.0 cc is injected, it can be seen that approximately 0.25 cc is injected at the higher pressures, but much more than half of the medication is injected during the shuttling, lower pressure phase.

A threaded poppet valve pressure adjustment face 91 may be threaded inwardly to increase or outwardly to decrease the pressure at which poppet valve 80 opens and closes. A special tool (not shown) is used to facilitate this adjustment.

Referring to FIGS. 8 and 8A, the syringe control system 18, which receives $CO_2$ pressure from poppet valve 80, will now be described. This system includes a dose compensator cylinder 94, a dose variation assembly 96 having a pressure piston 98 mounted thereto, an inner cylinder 100, a rearward outer cylinder 102, and a forward outer cylinder 104. So-called U-cup seals 99 and 101 will prevent pressure leakage between the stages of the syringe control system. The $CO_2$ pressure entering the syringe control system 18 causes the entire rearward outer cylinder 102 to shift forwardly or to the right in FIG. 8, against the compressive action of a light helical spring 97. Rearward outer cylinder 102 continues to shift until its forward end contacts the rear end of forward outer cylinder 104, which is about ⅛–3/16 inch into its travel. At this point, inner cylinder 100 continues to move in a forward direction for approximately another 1–½ inch, for a total travel of approximately 1¼ inches. This independent movement of the inner cylinder generally corresponds with the point that the shuttling begins in the cartridge pressure control system 14. Thus, the independent movement of inner cylinder 100 cooperates with the shuttling action to provide a reduced, substantially constant but lower second pressure phase to the injector. At this point, spring 97 will have bottomed out and immediately thereafter the controller will cause the solenoid valve to shut off $CO_2$ pressure.

Dose compensator cylinder 94 travels with inner cylinder 100 and rearward outer cylinder 102 in their above-described forward motion. Dose compensator cylinder 94 is a generally cylindrical member having a soft rubber bumper at the rear end thereof (not shown due to its small dimensions), and a centrally disposed axially extending channel 108 with an entry segment 110 at the rear end thereof, as shown best in FIG. 8. This entry segment 110 selectively interconnects channel 108 with fluid pressure from poppet valve 80. An O-ring 112 is provided on dose compensator cylinder 94 to prevent the flow of fluid pressure along the outer surface of the cylinder. A seal 114 is provided at the forward end of the dose compensator cylinder to minimize any leakage between the inner cylinder wall defining channel 108 and pressure piston 98.

The purpose of the dose compensator cylinder system is to account for the fact that pressure will tend to act somewhat differently on the syringe control system 18 when there is a greater or lesser amount of medication in the syringe. Because pressure piston 98 will move forwardly and rearwardly within channel 108 as the dosage is decreased and increased, respectively, thereby increasing and decreasing, respectively, the size of a chamber defined within channel 108 behind piston 98, this accommodation is made.

A helical spring 115 is positioned between dose compensator cylinder 94 and dose variation assembly 96 as shown in FIG. 8. Spring 115 provides a suitable amount of pressure which is passed onto syringe 126 and the medication provided therein to make sure that no air is in the system. With such a forward biasing of the syringe, the amount of medication in the syringe can be measured. As will be described below, if the dose variation assembly 96 is too far forward or to the right in FIG. 8, which indicates that there is an insufficient amount of medication in the syringe, then an interlock will prevent the apparatus from firing. This condition is sensed by a dose indicator flag 106 disposed in a dose indicator optical interrupter space 107. Dose indicator flag 106 is mounted to a cylindrical dose variation compensator 120 so that the position of the flag generally corresponds to the amount of medication in the syringe. When there is sufficient medication in the syringe, flag 106 will block infrared light from passing across space 107 from an illuminator (not shown) to a receptor (not shown). When there is an insufficient amount of medication in the syringe, spring 115 will cause flag 106 to be shifted to the right, withdrawing the flag from space 107 and permitting IR light to pass from the illuminator to the receptor, which will send a signal to the controller, thereby lighting a warning lamp and preventing the apparatus from entering its initiation phase.

It is possible that micro switches, magnetic switches, or other conventional position sensors (not shown) may be utilized in place of the optical interrupter described above.

Dose variation assembly 96 permits the dosage to easily be adjusted in ¼ cc increments (see FIG. 9). This is done through the use of a thumb-nail manipulator 118 which extends radially outwardly from the unit and which is mounted by a lock nut 111 to an axially extending rod 113 which is threaded into dose variation compensator 120. The dose variation compensator has a generally semi-spherical protrusion 122 mounted on it, and it is surrounded by a cylindrical jacket 123 shown best in FIG. 9. This jacket 123 has four circumferentially extending slots 125 interconnected by a single axially extending slot 127, the four slots being adapted to selectively receive semi-circular protrusion 122. Partitions 124 are disposed between and define the four slots. FIG. 9 shows that the partitions are relatively narrow in their circumferential dimensions, so that with only a 40–45° twist of compensator 120 with thumbnail manipulator 118, semi-spherical protrusion 122 can clear the adjacent partition, and under the pressure from springs 115, will be biased forwardly through axially extending slot 127 into the next adjacent slot 125, thereby adjusting the dosage by ¼ cc. If the thumbnail manipulator 118 has not been released, then the protrusion can selectively be guided over to another one of the four slots, depending upon the desired dosage. Once positioned, releasing the thumbnail manipulator permits a series of rotational biasing springs 119 to cause dose variation compensator 120 to rotate, which in turn moves the protrusion into one of the four slots 125.

The syringe 126 is shown best in FIG. 10. It includes an ampule 128 and a plunger 130. The end of the plunger includes a radially extending notch 132 which is interconnected with an axial slot 127 which is sized to fit onto rod 113 extending from dose variation compensator 120. A flared end 134 on the plunger is designed to abut the forward end of dose variation compensator 120. Thus, the axial drive force imparted to the compensator by rearward outer cylinder 102 and inner cylinder 100 will cause the plunger to drive forwardly, forcing medication out of the syringe. The syringe also includes a pair of opposed flanges 129 disposed adjacent the forward end thereof. The syringe ampule 128 includes a small injection aperture 20 at the forward end. Aperture 20 is typically 0.0045 inch in diameter, although it may be as large as 0.014 inch, depending upon the subcutaneous injection depth which is desired.

Syringe 126 fits into the apparatus by merely inserting the syringe through collar 9 in the front end of the apparatus, and pushing it in. When it is most of the way in, pressure from spring 115 will be felt. When it bottoms out against a wave spring 131, the syringe is rotated approximately 90 degrees so that flanges 129 are engaged within the syringe collar 9 as shown in FIG. 8B. As the syringe is rotated that 90 degrees, it engages a pin 133 which rotates with it. Once this pin 133 is rotated, it depresses a syringe lock micro switch 140, which sends a signal to the controller that the syringe has been properly installed. If this syringe lock micro switch is not depressed, the controller will light a warning lamp and prevent the apparatus from entering its initiation phase.

Figure 11:
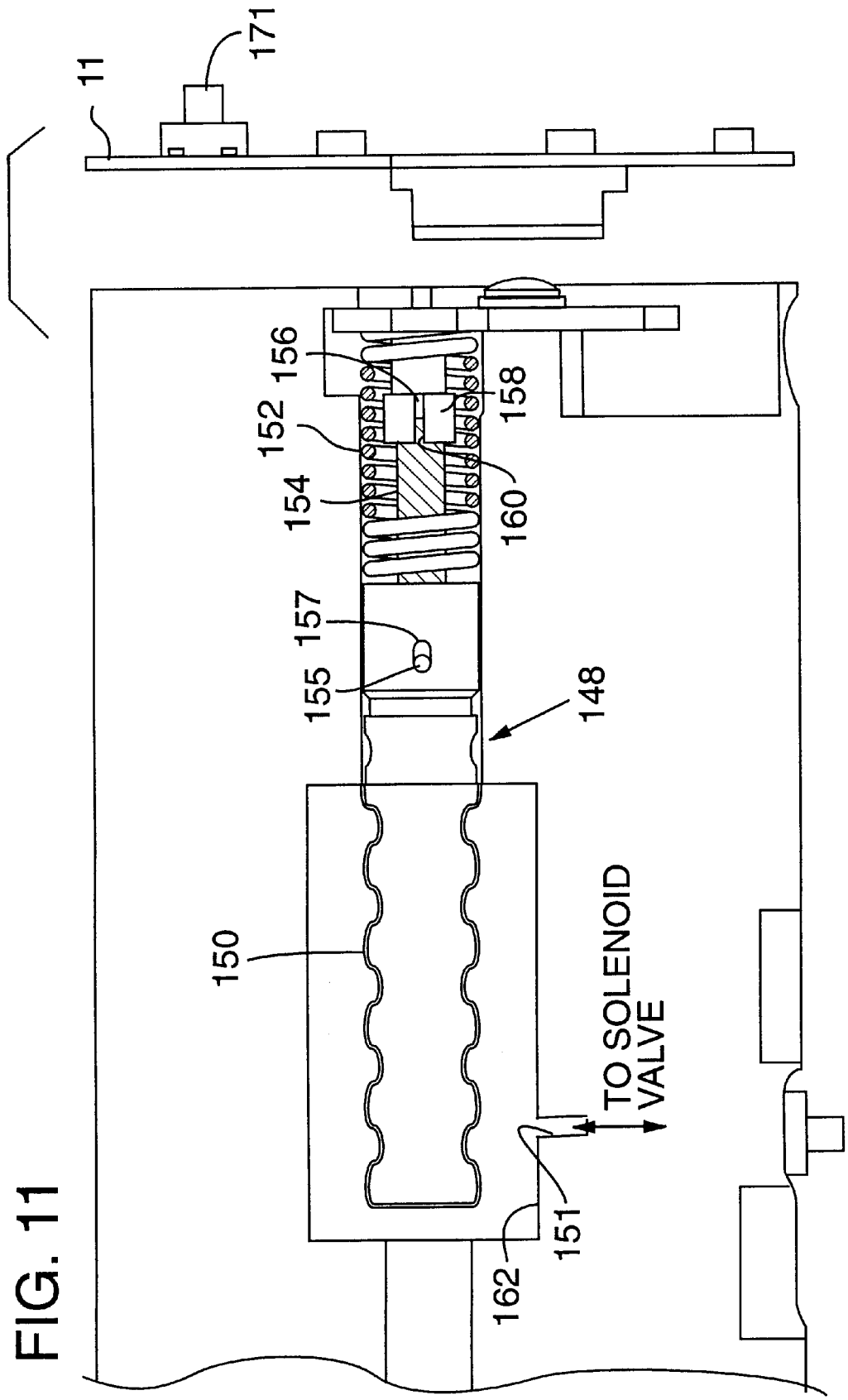
FIG. 11 is a side elevation sectional view of the pressure switch of the embodiment of FIG. 1.

A pressure switch 148 is disposed midway between and to the side of the portions of the apparatus which house the cartridge pressure control system 14 and the syringe control system 18, as shown best in FIG. 5. Referring now to FIG. 11, pressure switch 148 includes a bellows 150, a spring 152 and a central rod 154 which terminates in a flag 156. Flag 156 is disposed within a stationary optical interrupter 158 which transmits infrared light across a space 160 much like the previously-described dose measurement optical interrupter. When the flag is disposed within the space, the light is interrupted and a collector (not shown), which otherwise receives light from an emitter (not shown), sends a signal to a controller.

Bellows 150 is subjected to $CO_2$ cartridge pressure because a port 151 interconnects an otherwise-sealed chamber 162 surrounding the bellows with the $CO_2$ pressure present within solenoid valve 54. The variations in pressure cause the bellows to expand and contract, causing rod 154 and flag 156 to move slightly forwardly and rearwardly in relation to optical interrupter 158. A pin 155 travels within a short slot 157 such that some contraction or expansion of the bellows is permitted without causing any displacement of flag 156. If the pressure is relatively high, the flag blocks the transmission of IR light across space 160, but if the pressure is not as high as it should be, spring 152 causes bellows 150 to extend slightly into chamber 162, thereby causing rod 154 to withdraw flag 156 from optical interrupter 158, permitting IR light to be conveyed to a collector. This sends a signal to the controller, which lights an appropriate warning lamp and terminates the initiation cycle.

It is possible that a pressure switch other than the above-described bellows/optical interrupter could be used. For example, it may be possible to use a helical or a spiral bourdon tube could be used in place of the bellows, and another type of switch other than the described optical interrupter.

To ensure that the apparatus is pressed up against the skin of the patient prior to activation of the apparatus, skin sensor 10 is provided. The skin sensor includes an extension rod 142 which is forwardly biased under the pressure of a skin sensor spring 144 to the extended position shown in FIG. 8. A soft plastic jacket 138 fits over the extension rod in the depicted embodiment. As the apparatus is sufficiently pressed against the skin of the patient, the extension rod is depressed against the pressure of the skin sensor spring, and a spring sensor micro switch 144 is contacted, sending an electronic signal to the controller to prevent termination of the initiation cycle. If the skin sensor is not sufficiently depressed, the controller lights a warning lamp and the initiation cycle is terminated. Skin sensor 10 thereby functions to prevent inadvertent or other discharge of the apparatus when the apparatus is not properly positioned against the skin, which may happen if the patient is reluctant or, again, physical dexterity problems make it difficult for the patient to properly position the apparatus.

Figure 12:
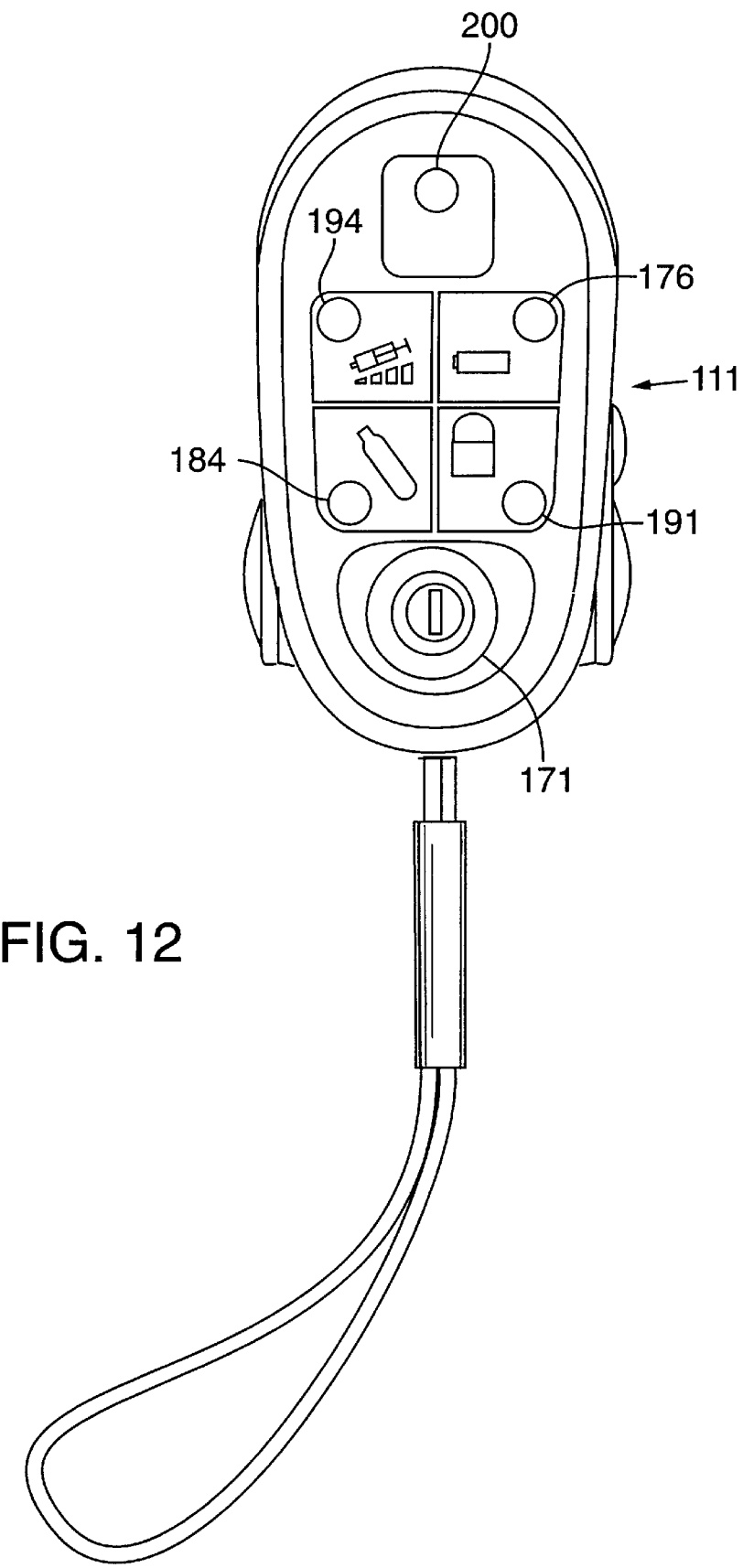
FIG. 12 is an enlarged view corresponding to that of FIG. 3.

Indicator panel 11, shown best in FIG. 12, includes the following red warning lamps: $CO_2$ pressure warning lamp 184; dose volume warning lamp 194; syringe lock warning lamp 19 1; and battery warning lamp 176. A green "ready" lamp 200 is also included, as is a power button 171.

Figure 13:
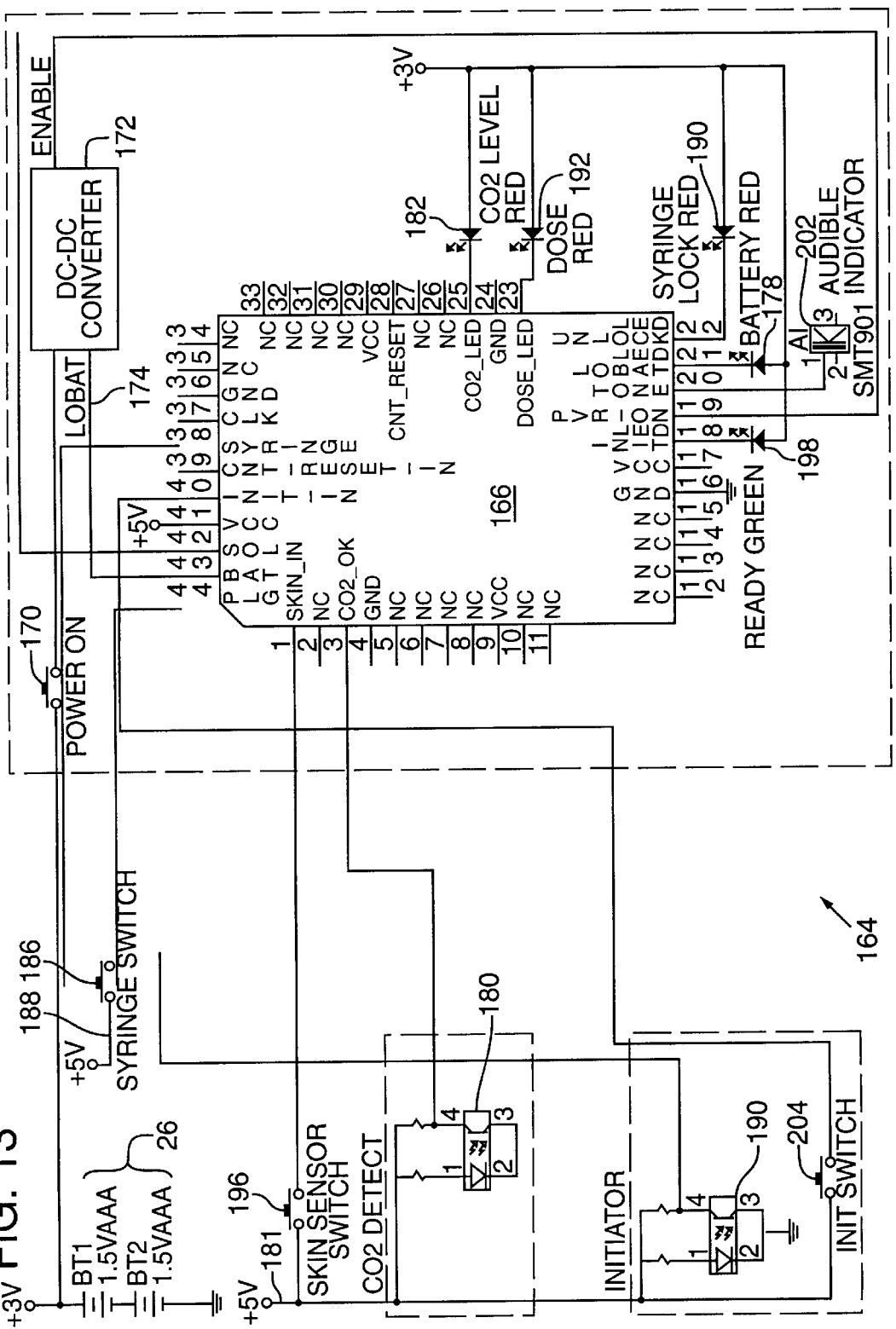
FIG. 13 is the logic circuit of the preferred embodiment of FIG. 1.

Reference will be made to the control circuit schematic, FIG. 13, as well as to the indicator panel 11 provided at the rear of the apparatus, and depicted in FIG. 12. The logic circuit, indicated generally with the numeral 164, selectively provides power to light the lamps of the indicator panel. Central to the circuit is controller 166 which in the preferred embodiment is an Atmel programmable logic device, designated as model ATF 1500L. This is a low power unit which can effectively control the operation of the apparatus while using a minimal amount of power so that the batteries do not have to be replaced very often.

As mention ed earlier, the apparatus includes a number of interlocks which prevent the unit from operating, and warn the operator in the event any one of a number of conditions is not satisfied. The logic circuit provides this capability, but before describing those features, reference will first be made to the general layout of the circuit.

The batteries, shown at 26, are mounted in series to provide 3 volts of DC power to the circuit. A power switch 70, which corresponds with power button 171 (see FIG. 12), controls the flow of power to a DC-DC converter 172, which converts the 3 volt charge to a 5 volt charge as needed elsewhere in the circuit. In the event there is low battery power, a signal is sent to the controller via line 174, and a red "battery" light 176 is activated in indicator panel 11 depicted in FIG. 12. This light is energized by an LED 178 which is connected to an active low pin in controller 166 which sends the 3 volt charge to ground upon a low battery signal from line 174, thereby energizing the LED and warning the operator that the batteries need to be replaced. This event prevents the initiation of the apparatus so that even if the operator ignores the light, the apparatus cannot be initiated. In the event there is sufficient battery power, voltage is provided to the controller to activate the apparatus.

Another one of the interlocks provides protection for insufficient $CO_2$ pressure. As described above, pressure switch 148 determines whether sufficient $CO_2$ pressure is sufficient. If it is, flag 156 will block light from passing through optical interrupter 158, and a transistor in a $CO_2$ detect subcircuit 180 will remain open. In this condition, the controller will sense the 5 volt charge coming in from line 181. If $CO_2$ pressure is insufficient, the flag will withdraw, permitting light to pass through the optical interrupter, which will then close the $CO_2$ detect subcircuit 180, thus grounding the 5 volt charge, which will be sensed by the controller. Simultaneously, an active low pin to which a $CO_2$ cartridge LED 182 is connected will ground that LED circuit, energizing that LED and activating a red $CO_2$ cartridge light 184 in indicator panel 11, as shown in FIG. 12. This event also causes the controller to prevent initiation of the apparatus even if the user ignores the indicator panel warning light 184.

Yet another interlock is provided to ensure that there is sufficient medication in ampule 128. A dose detect subcircuit 190, very similar to $CO_2$ detect subcircuit 180, is provided. Dose detect subcircuit 190 is provided with a 5 volt charge from line 181, and if a sufficient dosage level is sensed by the dose indicator optical interrupter, a transistor in the dose detector subcircuit will remain open and the controller will sense 5 volts. If the dose is insufficient, the transistor will close and the controller will sense the absence of the 5 volt charge. In that event, a red volume warning lamp 194 is lit in indicator panel 11 by a dose detector LED 192. This light is connected to an active low pin in the controller which sends the 3 volt charge to ground, thereby activating the LED. Unless the dose is sufficient, this dose interlock will warn the user at the indicator panel and will prevent the apparatus from initiating.

Yet another interlock is provided with a syringe switch 186 which ensures that the syringe is properly locked into positioned in the apparatus before the unit is initiated. As noted previously, this condition is sensed by syringe lock micro switch 140. Syringe switch 186 receives a 5 volt charge from line 188. If the syringe is properly locked in place, the syringe switch will be closed. In this condition, the controller senses the 5 volt charge, and the apparatus is ready for initiation. If the syringe is not properly locked in place, a syringe lock LED 193 will activate a red syringe lock warning lamp 191 and the controller will prevent the apparatus from entering its initiation cycle.

If all of the conditions have been met (other than the next-to-be-described skin sensor), the controller operates to flash a green "ready" light 200 in indicator panel 11.

The skin sensor interlock will now be described. A skin sensor switch 196 is provided off 5 volt line 181. In order to initiate the apparatus, skin sensor 10 must be depressed, thereby closing skin sensor switch 196 and sending a 5 volt charge to the controller. Unless this charge is sensed by the controller, the apparatus will be prevented from entering its initiation cycle. When the charge is received, showing that everything is ready for initiation, skin sensor LED 198 will provide a steady activation of the green "ready" light 200 in indicator panel 11, and an audible indicator 202 will emit a beep.

An initiator switch 204 is also provided off 5 volt line 181, which is closed by depressing indicator panel initiator button 171. If all of the foregoing conditions have been satisfied, closing of the initiator switch will send a 5 volt charge to the controller, which in turn sends power to solenoid valve 54 to cause $CO_2$ pressure to inject medication into the patient. If any of the foregoing conditions have not been satisfied, the appropriate warning lights will be lit, and the controller will prevent the apparatus from entering its initiation cycle.

Operation of the Depicted Embodiment

In order to use the apparatus depicted in the figures, the user first must install batteries 26 into battery case 146. This is done by opening cartridge access door 6 and removing the $CO_2$ cartridge if there is one in place. Next, $CO_2$ cartridge 12 is installed into cartridge receptacle 28. Once the cartridge is in place, cartridge access door 6 is pivoted closed. The action of the cartridge door mechanism causes pierce block 42 to shift rearwardly and under the action of springs 52, forward seat 30 pushes rearwardly on the cartridge, which causes the rear of the cartridge to be pushed down so that piercing pin 36 pierces the rear end of the cartridge.

Breach of the $CO_2$ cartridge causes pressurized $CO_2$ gas to pass through piercing pin 36, filter 56, and axial conduit 58 to space 60 and spring chamber 62. Pressurized gas also flows around piston 76. Because there is greater surface area on the forward side of the piston than on the rear side, solenoid seal 66 is held against solenoid seat 68 to prevent the flow of pressurized gas into rear conduit 59.

Of course, it is not always necessary to replace the batteries and the $CO_2$ cartridge. The batteries should last for an extended period, and the $CO_2$ cartridge will last for approximately 6 to 8 injections. In any event, either before or after they are replaced, the dose adjust mechanism is set, and the syringe is filled with medication and placed into the apparatus.

Before insertion of the syringe into the apparatus, thumbnail manipulator 118 is adjusted to the appropriate dosage by first sliding open the dose adjustment door 8, and then turning the manipulator slightly and moving it axially to the right to decrease and to the left to increase the dosage, in ¼ cc increments. The dose adjustment door is then closed and the apparatus is ready to receive the syringe.

The syringe 126 is first filled with the desired amount of medication, is purged of air and is then mounted in the apparatus. The syringe is normally over-filled so that there is somewhat more medication in the ampule than the apparatus dosage setting, just to make sure the ampule is not under-filled. Once the syringe has been filled to an appropriate level, it is inserted through collar 9 in the front of the apparatus. As the syringe is slid into place, the pressure from spring 115 will be felt, and as the syringe is pushed beyond that point, wave spring 131 will also be felt. At that point the syringe is rotated 90 degrees and engaged.

The apparatus is now ready to have the power turned on, so this is done by depressing power button 171 on indicator panel 148. Once the power is on, the operator can check to see if $CO_2$ pressure warning lamp 184 is lit, and if it is, then the pressure switch 148 has determined that there is insufficient pressure, and the $CO_2$ cartridge needs to be replaced. Similarly, if the syringe has not been properly installed, the red syringe lock lamp 191 on the indicator panel will be lit; if there is insufficient medication in the syringe as determined by the dose indicator, the red dose volume lamp 194 will be lit; and if there is insufficient battery power, the red battery warning lamp 176 will be lit. If all conditions are satisfied, the apparatus is ready for use, and the green "ready" light 200 will flash intermittently.

To initiate the injection, the user presses the front end of the apparatus against the skin, which depresses skin sensor 10. This causes the green "ready" lamp 200 on the indicator panel to light, and the audible alarm to sound, informing the user that the apparatus is ready to initiate. Depression of initiator button 171 causes the initiator switch to close if all four of the aforementioned conditions are met. This in turn activates solenoid valve 54 which permits pressurized $CO_2$ to rush into gas reservoir 84, causing poppet valve 80 to lift, sending pressure into the syringe control side of the apparatus. This pressure drives rearward outer cylinder 102 and inner cylinder 100 forward, which causes rod 123 to drive syringe plunger 130, forcing medication out of syringe aperture 20 and through the skin of the patient at a highly elevated pressure. Poppet valve 80 then enters its shuttling mode, during which most of the medication is injected at a somewhat lower pressure. Once inner cylinder 100 bottoms out against spring 97, injection is complete and solenoid valve 54 is closed. After each injection, however, $CO_2$ pressure is maintained in the solenoid, upstream of solenoid piston 76, so that the unit is immediately ready for another injection once the syringe is replaced.

I claim:

1. A needleless injector comprising:
   a needleless syringe installed in the injector for holding medication prior to injection, the syringe including an injection aperture at a forward end thereof;
   a syringe plunger slidably mounted to a rear end of the syringe for forcing medication out of the syringe aperture;
   a syringe plunger drive mechanism providing power to drive the syringe plunger and thereby force medication out of the syringe;
   a drive control mechanism for controlling the operation of the drive mechanism, the drive control mechanism including a warning system which warns the user if any one of a plurality of pre-injection conditions is not met, an interlock system which prevents injection from taking place if any one of the plurality of pre-injection conditions are not met, and a sensing system which senses whether the plurality of pre-injection conditions is not met and conveys a signal to the warning and interlock systems informing as to whether all of the pre-injection conditions are met.

2. The injector of claim 1 wherein the sensing system senses whether the syringe is properly installed in the injector.

3. The injector of claim 2 wherein the system for sensing whether the syringe is properly installed includes a microswitch disposed adjacent the syringe which closes upon proper installation of the syringe, thereby deactivating the warning system and the interlock system and permitting injection.

4. The injector of claim 1 wherein the drive mechanism includes a compressed gas drive, and wherein the sensing system senses whether there is sufficient compressed gas pressure, and the interlock system prevents injection from taking place if there is insufficient compressed gas pressure.

5. The injector of claim 4, further comprising a sensor, and wherein the system for sensing whether there is sufficient compressed gas pressure and the interlock system for preventing injection if there is insufficient gas pressure include a pressure switch having a bellows which is displaceable based upon the compressed gas pressure, and a flag member mounted to the bellows which moves into and out of alignment with the sensor based upon the displacement of the bellows, and thereby controlling the activation of a signal in the event of inadequate pressure to the bellows.

6. The injector of claim 5 wherein the bellows is displaced a predetermined amount before the flag member is moved.

7. The injector of claim 1 wherein the drive control mechanism includes an electrical source for providing electrical power, wherein the sensing system senses whether the electrical source is providing sufficient power, and wherein the interlock system receives a signal from the sensing source to permit or prevent injection.

8. The injector of claim 1 wherein the sensing system senses whether there is sufficient medication in the syringe, and the interlock system prevents injection from taking place if there is insufficient medication in the syringe.

9. The injector of claim 8, wherein the interlock system for preventing injection when there is insufficient medication in the syringe includes a flag member, the position of which varies in relation to the position of the syringe plunger which directly corresponds to the amount of medication in the syringe, the flag member moving into and out of alignment with the sensor for sensing the position of the syringe, thereby controlling a signal in the event of insufficient medication in the syringe.

10. The injector of claim 9, further including a spring against which the syringe plunger is forced as the syringe is installed in the injector to expel any air therefrom.

11. The injector of claim 1 wherein the syringe plunger drive mechanism initially drives a first portion of the medication out of the syringe at a first, elevated pressure, and then drives a second portion of the medication out of the syringe at a lower, substantially constant, second pressure.

12. The injector of claim 11 wherein the syringe plunger drive mechanism includes a valve having a substantially planar face which lifts against the action of a spring when subjected to a predetermined gas pressure to provide the first pressure to the syringe, at which time the valve approaches a closed position and then oscillates in rapid succession to provide the second pressure to the syringe.

13. The injector of claim 1, wherein the drive mechanism provides a compressed gas drive to the syringe plunger.

14. The injector of claim 13 wherein the compressed gas drive is provided by a compressed gas cylinder, and further comprising a piercing pin mounted to the injector, and a compressed gas cartridge access door which opens to permit insertion of the cartridge into a cartridge receptacle defined in the injector, the access door also closing against a spring to effect relative movement between the cartridge and the piercing pin to pierce the cartridge.

15. The injector of claim 14 wherein the cartridge access door pivotally opens and closes, the closure of the door exerts a force on the cartridge to force the cartridge against the piercing pin, the spring being compressed further if a larger cartridge is used, and being compressed less if a smaller cartridge is used.

16. The injector of claim 14 wherein the piercing of the cartridge permits compressed gas to pass into a solenoid valve disposed in the injector, the opening of which permits compressed gas to drive the syringe plunger.

17. The injector of claim 16 wherein the solenoid includes a reciprocable piston which selectively seals a conduit and which compressed gas surrounds upon the piercing of the cartridge, and which when the solenoid valve is opened shifts to unseal the conduit to permit compressed gas to flow therethrough to drive the syringe plunger.

18. The injector of claim 17 further comprising a poppet valve mounted in the injector in fluid connection with the conduit, the poppet valve being selectively maintained in a closed position by a spring and wherein the opening of the solenoid valve causes compressed gas passing through the conduit to flow to the poppet valve and exert pressure thereon against the pressure of the spring, so that when a predetermined pressure is reached the poppet valve opens to permit a rush of compressed gas to flow therethrough to drive the syringe plunger.

19. The injector of claim 18 wherein the poppet valve spring pressure is set such that the rush of compressed gas through the poppet valve causes pressure on the poppet valve by the compressed gas to drop, causing the poppet valve to momentarily close, causing the compressed gas pressure on the poppet valve to be increased to open the poppet valve, and wherein this opening and closing occurs in rapid succession to provide a substantially constant, lower drive pressure to the plunger following the initial rush of compressed gas which provides a higher drive pressure to the plunger.

20. The injector of claim 13, further comprising a dose adjustment mechanism which permits the medication dosage to be adjusted.

21. The injector of claim 20 wherein the dose adjustment mechanism is in the form of a plunger drive piston which can be adjusted toward and away from the syringe to permit less or more medication, respectively, to be loaded into the syringe.

22. The injector of claim 21 wherein the plunger drive piston includes an axial slot with a plurality of contiguous circumferential slots, and a protrusion which can be guided into any of the circumferential slots and thereby control the position of the plunger with respect to the syringe to determine the amount of medication held in the syringe for subsequent injection.

23. The injector of claim 21, further comprising a dose compensator defining a dose compensation chamber which is enlarged and reduced as the amount of medication is decreased and increased, respectively, the dose compensation chamber being in fluid communication with the drive mechanism.

24. The injector of claim 1 wherein the drive mechanism provides compressed gas to drive the syringe, the injector further comprising an electric power source for providing power for controlling the operation of the injector, and wherein the plurality of pre-injection conditions include any one of the following: insufficient compressed gas pressure; insufficient electric power; and insufficient medication in the injector.

* * * * *